United States Patent
Zhang et al.

(10) Patent No.: US 11,104,889 B2
(45) Date of Patent: Aug. 31, 2021

(54) PHI29 DNA POLYMERASE MUTANT HAVING INCREASED THERMAL STABILITY AND USE THEREOF

(71) Applicant: MGI Tech Co., Ltd., Shenzhen (CN)

(72) Inventors: Zhougang Zhang, Shenzhen (CN); Huanhuan Liu, Shenzhen (CN); Yue Zheng, Shenzhen (CN); Yujun Zhou, Shenzhen (CN); Xing Liu, Shenzhen (CN); Yuliang Dong, Shenzhen (CN); Chongjun Xu, Shenzhen (CN); Wenwei Zhang, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 0 days.

(21) Appl. No.: 16/633,942

(22) PCT Filed: Aug. 9, 2017

(86) PCT No.: PCT/CN2017/096599
§ 371 (c)(1),
(2) Date: Jan. 24, 2020

(87) PCT Pub. No.: WO2019/019222
PCT Pub. Date: Jan. 31, 2019

(65) Prior Publication Data
US 2020/0208126 A1 Jul. 2, 2020

(30) Foreign Application Priority Data
Jul. 28, 2017 (CN) .......................... 201710630969.0

(51) Int. Cl.
*C12N 9/12* (2006.01)
(52) U.S. Cl.
CPC .... *C12N 9/1252* (2013.01); *C12Y 207/07007* (2013.01)
(58) Field of Classification Search
CPC .............................. C12N 9/1252; C12N 9/12; C12Y 207/07007; C12P 19/34
See application file for complete search history.

(56) References Cited

U.S. PATENT DOCUMENTS

| | | |
|---|---|---|
| 2015/0218535 A1 | 8/2015 | Kamtekar et al. |
| 2016/0237412 A1* | 8/2016 | Kamtekar ...... C12Y 207/07007 |
| 2016/0348166 A1* | 12/2016 | Kamtekar .............. C12Q 1/686 |
| 2017/0015980 A1 | 1/2017 | Skirgaila et al. |
| 2017/0159033 A1* | 6/2017 | Kamtekar ................ C12M 1/42 |

OTHER PUBLICATIONS

Freire et al., GenBank accession No. CAA65712, Apr. 18, 2005.*
Lopes Ferreira et al., Gen Bank accession No. CUU51220, May 1, 2017.*
Oeser et al., Gen Bank accession No. P22373, Feb. 1, 1994.*
Hertel et al., GenBank accession No. ASR76790, Aug. 9, 2017.*
Witkowski et al., Biochemistry 38:11643-11650, 1999.*
Tang et al., Phil Trans R Soc B 368:Mar. 18, 2012, 1-10, 2013.*
Seffernicketal., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Lian, D., et al. "Research Advances in the Latest Application of phi29 DNA Polymerase" Pharmaceutical Biotechnology,Apr. 15, 2016, 23(2), ISSN: 1005-8915, see pp. 150-154., English Abstract.
De Vega, M. et al. "29 DNA Polymerase Residue Ser (122), a Single-stranded DNA Ligand for 3'-5' Exonucleolysis, is Required to Interact with the Terminal Protein" Journal of Biological Chemistry, Oct. 30, 1998, 273(44), ISSN: 0021-9258, see pp. 28966-28977.
International Search Report issued for PCT/CN2017/096599, dated Apr. 4, 2018.
Written Opinion of the International Searching Authority issued for PCT/CN2017/096599, dated Apr. 4, 2018.

* cited by examiner

*Primary Examiner* — Delia M Ramirez
(74) *Attorney, Agent, or Firm* — Westman, Champlin & Koehler, P.A.; Z. Peter Sawicki; Amanda M. Prose

(57) ABSTRACT

Provided are a group of phi29 DNA polymerase mutants having increased thermal stability and use thereof. The phi29 DNA polymerase mutants are proteins obtained by performing point mutation A and/or point mutation B and/or point mutation C on phi29 DNA polymerase, the point mutation A meaning that an amino acid residue M at position 97 of the phi29 DNA polymerase is mutated to other amino acid residue, the point mutation B meaning that an amino acid residue L at position 123 of the phi29 DNA polymerase is mutated into other amino acid residue, and the point mutation C meaning that an amino acid residue E at position 515 of the phi29 DNA polymerase is mutated to other amino acid residue. The stability of the phi29 DNA polymerase mutants is higher than that of a wild-type phi29 DNA polymerase.

5 Claims, No Drawings
Specification includes a Sequence Listing.

SEQUENCE LISTING

<160> NUMBER OF SEQ ID NOS: 21

<210> SEQ ID NO 1
<211> LENGTH: 575
<212> TYPE: PRT
<213> ORGANISM: Artificial Sequence
<220> FEATURE:
<223> OTHER INFORMATION: Amino acid sequence of wild-type phi29 DNA
      polymerase of Bacillus subtilis

<400> SEQUENCE: 1

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

```
Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 1728
<212> TYPE: DNA
<213> ORGANISM: Artificial Sequence
<220> FEATURE:
<223> OTHER INFORMATION: Nucleotide sequence of wild-type phi29 DNA
      polymerase of Bacillus subtilis

<400> SEQUENCE: 2
atgaaacata tgccgcgcaa aatgtatagc tgcgactttg aaaccaccac caaagtggaa      60
gattgccgcg tttgggcgta tggctatatg aacatcgaag accacagcga atacaaaatt     120
ggcaacagcc tggatgaatt tatggcgtgg gtgctgaaaa ttcaggcgga tctgtatttt     180
cacaacctga atttgacgg cgcgttcatt attaactggc tggaacgcaa cggctttaaa     240 tggagcgcg atggcttacc gaacacctat aacaccatta ttagccgcat gggccagtgg     300
tatatgattg atatctgcct gggctataaa ggcaaacgca agattcatac cgtgatctat     360
gatagcctga gaaactgcc gtttccggtg aaaaaaatcg cgaaggactt taaactgacc     420
gtgctgaaag cgatattga ctaccataaa gaacgcccgg tgggctataa aattaccccg     480
gaggaatatg cgtacatcaa gaacgacatc cagattattg cggaagcgct gctgattcag     540
tttaaacagg gcctggatcg tatgaccgcg ggtagcgata gcctgaaagg ctttaaggac     600
attatcacca ccaagaagtt caagaaagtg tttccgaccc tgagcctggg cctggataaa     660
gaagtgcgct atgcgtatcg cggtggcttt acctggctga cgatcgctt taaggaaaag     720 gaaattggcg aaggcatggt gtttgatgtg aacagcctgt atccggcgca gatgtatagc     780
```

```
cgcctgctgc cgtatggtga accgattgtg tttgaaggca agtatgtgtg ggatgaagat    840
tatccgctgc acattcagca tattcgctgc gaattcgaac tgaaggaagg ctatattccg    900
accattcaga ttaaacgcag ccgcttttat aaaggcaacg agtacctgaa aagcagcggc    960
ggcgaaattg cggatctgtg gctgagcaac gtggatctgg aactgatgaa agaacactac   1020
gatctgtaca acgtggaata tatcagcggc ctgaaattta aagcgaccac cggcctgttt   1080
aaggacttta tcgacaagtg gacctacatt aaaaccacca gcgaaggcgc gattaaacag   1140
ctggcgaaac tgatgctgaa cagcctgtat ggcaaatttg cgagcaaccc ggatgttacc   1200
ggcaaagtgc cgtatctgaa agaaaacggc gcgctgggct ttcgtttagg cgaagaggaa   1260
accaaagatc cggtgtatac cccgatgggc gtgtttatta ccgcgtgggc gcgctatacc   1320
accattaccg cggcgcaggc gtgttatgat cgcattatct attgcgatac cgatagcatt   1380
catctgaccg gcaccgaaat tccggatgtg atcaaagata ttgtggaccc gaaaaaactg   1440
ggctattggg cgcatgaaag caccttaaa cgcgcgaaat atctgcgcca gaaaaacctat  1500 atccaggaca tctacatgaa agaggtggat ggcaaactgg ttgaaggcag cccggatgat   1560
tataccgata ttaagttcag cgtgaaatgc gcgggcatga ccgataaaat taagaaggaa   1620
gtgaccttcg agaactttaa agtgggcttt agccgcaaaa tgaaaccgaa accggttcag   1680
gtgcctggcg tgttgttct ggtggatgat accttcacca tcaagtga                1728

<210> SEQ ID NO 3
<211> LENGTH: 25
<212> TYPE: DNA
<213> ORGANISM: Artificial Sequence
<220> FEATURE:
<223> OTHER INFORMATION: 141 RCA Primer

<400> SEQUENCE: 3
tcctaagacc gcttggcctc cgact                                           25

<210> SEQ ID NO 4
<211> LENGTH: 38
<212> TYPE: DNA
<213> ORGANISM: Artificial Sequence
<220> FEATURE:
<223> OTHER INFORMATION: Forward primer for point mutation 97H

<400> SEQUENCE: 4
caccattatt agccgccatg gccagtggta tatgattg                             38

<210> SEQ ID NO 5
<211> LENGTH: 38
<212> TYPE: DNA
<213> ORGANISM: Artificial Sequence
<220> FEATURE:
<223> OTHER INFORMATION: Reverse primer for point mutation 97H

<400> SEQUENCE: 5
caatcatata ccactggcca tggcggctaa taatggtg                             38

<210> SEQ ID NO 6
<211> LENGTH: 38
<212> TYPE: DNA
<213> ORGANISM: Artificial Sequence
<220> FEATURE:
<223> OTHER INFORMATION: Forward primer for point mutation 97A

<400> SEQUENCE: 6
caccattatt agccgcgcgg gccagtggta tatgattg                             38
```

<210> SEQ ID NO 7
<211> LENGTH: 38
<212> TYPE: DNA
<213> ORGANISM: Artificial Sequence
<220> FEATURE:
<223> OTHER INFORMATION: Reverse primer for point mutation 97A

<400> SEQUENCE: 7
caatcatata ccactggccc gcgcggctaa taatggtg                    38

<210> SEQ ID NO 8
<211> LENGTH: 38
<212> TYPE: DNA
<213> ORGANISM: Artificial Sequence
<220> FEATURE:
<223> OTHER INFORMATION: Forward primer for point mutation 97K

<400> SEQUENCE: 8
caccattatt agccgcaaag gccagtggta tatgattg                    38

<210> SEQ ID NO 9
<211> LENGTH: 38
<212> TYPE: DNA
<213> ORGANISM: Artificial Sequence
<220> FEATURE:
<223> OTHER INFORMATION: Reverse primer for point mutation 97K

<400> SEQUENCE: 9
caatcatata ccactggcct ttgcggctaa taatggtg                    38

<210> SEQ ID NO 10
<211> LENGTH: 38
<212> TYPE: DNA
<213> ORGANISM: Artificial Sequence
<220> FEATURE:
<223> OTHER INFORMATION: Forward primer for point mutation 123K

<400> SEQUENCE: 10
ccgtgatcta tgatagcaaa aagaaactgc cgtttccg                    38

<210> SEQ ID NO 11
<211> LENGTH: 38
<212> TYPE: DNA
<213> ORGANISM: Artificial Sequence
<220> FEATURE:
<223> OTHER INFORMATION: Reverse primer for point mutation 123K

<400> SEQUENCE: 11
cggaaacggc agtttctttt tgctatcata gatcacgg                    38

<210> SEQ ID NO 12
<211> LENGTH: 38
<212> TYPE: DNA
<213> ORGANISM: Artificial Sequence
<220> FEATURE:
<223> OTHER INFORMATION: Forward primer for point mutation 123F

<400> SEQUENCE: 12
ccgtgatcta tgatagcttt aagaaactgc cgtttccg                    38

<210> SEQ ID NO 13
<211> LENGTH: 38
<212> TYPE: DNA
<213> ORGANISM: Artificial Sequence
<220> FEATURE:

<223> OTHER INFORMATION: Reverse primer for point mutation 123F

<400> SEQUENCE: 13
cggaaacggc agtttcttaa agctatcata gatcacgg     38

<210> SEQ ID NO 14
<211> LENGTH: 38
<212> TYPE: DNA
<213> ORGANISM: Artificial Sequence
<220> FEATURE:
<223> OTHER INFORMATION: Forward primer for point mutation 123I

<400> SEQUENCE: 14
ccgtgatcta tgatagcatt aagaaactgc cgtttccg     38

<210> SEQ ID NO 15
<211> LENGTH: 38
<212> TYPE: DNA
<213> ORGANISM: Artificial Sequence
<220> FEATURE:
<223> OTHER INFORMATION: Reverse primer for point mutation 123I

<400> SEQUENCE: 15
cggaaacggc agtttcttaa tgctatcata gatcacgg     38

<210> SEQ ID NO 16
<211> LENGTH: 38
<212> TYPE: DNA
<213> ORGANISM: Artificial Sequence
<220> FEATURE:
<223> OTHER INFORMATION: Forward primer for point mutation 123H

<400> SEQUENCE: 16
ccgtgatcta tgatagccat aagaaactgc cgtttccg     38

<210> SEQ ID NO 17
<211> LENGTH: 38
<212> TYPE: DNA
<213> ORGANISM: Artificial Sequence
<220> FEATURE:
<223> OTHER INFORMATION: Reverse primer for point mutation 123H

<400> SEQUENCE: 17
cggaaacggc agtttcttat ggctatcata gatcacgg     38

<210> SEQ ID NO 18
<211> LENGTH: 33
<212> TYPE: DNA
<213> ORGANISM: Artificial Sequence
<220> FEATURE:
<223> OTHER INFORMATION: Forward primer for point mutation 515P

<400> SEQUENCE: 18
ggatggcaaa ctggttccgg gcagcccgga tgv     33

<210> SEQ ID NO 19
<211> LENGTH: 32
<212> TYPE: DNA
<213> ORGANISM: Artificial Sequence
<220> FEATURE:

```
<223> OTHER INFORMATION: Reverse primer for point mutation 515P

<400> SEQUENCE: 19
catccgggct gcccggaacc agtttgccat cc                                32

<210> SEQ ID NO 20
<211> LENGTH: 32
<212> TYPE: DNA
<213> ORGANISM: Artificial Sequence
<220> FEATURE:
<223> OTHER INFORMATION: Forward primer for point mutation 515G

<400> SEQUENCE: 20
ggatggcaaa ctggttggcg gcagcccgga tg                                32

<210> SEQ ID NO 21
<211> LENGTH: 32
<212> TYPE: DNA
<213> ORGANISM: Artificial Sequence
<220> FEATURE:
<223> OTHER INFORMATION: Reverse primer for point mutation 515G

<400> SEQUENCE: 21
catccgggct gccgccaacc agtttgccat cc                                32
```

PHI29 DNA POLYMERASE MUTANT HAVING INCREASED THERMAL STABILITY AND USE THEREOF

CROSS-REFERENCE TO RELATED APPLICATIONS

This application is a US National Phase application based upon PCT Application No. PCT/CN2017/096599 filed with the National Intellectual Property Administration of P. R. China on Aug. 9, 2017, which claims priority to Chinese Patent Application No. 201710630969.0 filed Jul. 28, 2017, the entire content of which are incorporated herein by reference.

FIELD

The present disclosure relates to a phi29 DNA polymerase mutant with improved thermal stability and application thereof.

BACKGROUND

Phi29 DNA polymerase, belonging to the family B DNA polymerase, is a DNA polymerase derived from *Bacillus subtilis* phi29 phage. The crystal structure of phi29 DNA polymerase shows that phi29 DNA polymerase has two unique domains, i.e. TPR1 and TPR2 domains, in addition to conserved domains Palm, Thumb, Finger and Exo which are contained in common family B DNA polymerases, in which such a TPR2 domain takes part in forming a narrow channel surrounding the downstream DNA strand template, making the double-stranded DNA dissociated; meanwhile, the Palm, Thumb, TPR1 and TPR2 domains constitute a circular structure which tightly binds to the upstream double strands newly formed by template strand. Due to its structural characteristics, the phi29 DNA polymerase has a specific high processivity, strong strand displacement activity and 3'-5' exonuclease correction activity, thus commonly used in thermostatic amplification process, such as Rolling Circle Amplification (RCA) of micro amount of circular plasmids, Multiple Displacement Amplification (MDA) of genome and the like, and further applied to steps of library preparation through high-throughput sequencing, strand displacement amplification and the like.

Phi29 DNA polymerase is a mesophile enzyme, with a poor thermal stability, which can be inactivated by heating at 65° C. for 10 minutes. In practice, the storage life of phi29 DNA polymerase product, effect of DNA amplification and sequencing and the like are often affected due to the poor thermal stability.

Regarding the improvement of thermal stability and optimization of amplification efficiency for phi29 DNA polymerase, the current research mainly focuses on aspects of 1) optimization of storage buffer or reaction buffer, such as adding some surfactants or compatible solutes, and 2) mutating the protein sequence of wild-type phi29 DNA polymerase or constructing a chimeric protein.

Although improvement on thermal stability of phi29 DNA polymerase has been achieved to some extent for existing technology and invention, the development on phi29 DNA polymerase with higher thermal stability is still needed. In one aspect, because mutation targeting thermal stability will affect function of other domains of polymerase thus further affecting downstream application, modification on phi29 DNA polymerase which is combined with different applications has practical significance. In another aspect, companies have a need to develop their own patented products to avoid the risk of patent infringement in view of commercial competition and restriction of patent rights.

SUMMARY

The object of the present disclosure is to provide a phi29 DNA polymerase mutant with improved thermal stability and application thereof.

The present disclosure in embodiments provides a protein, which is obtained by subjecting a phi29 DNA polymerase shown in SEQ ID NO: 1 to point mutation A and/or point mutation B and/or point mutation C, wherein the point mutation A is the mutation of amino acid residue Methionine (M) at position 97 of the phi29 DNA polymerase to other amino acid residues; the point mutation B is the mutation of amino acid residue Leucine (L) at position 123 of the phi29 DNA polymerase to other amino acid residues; and the point mutation C is the mutation of amino acid residue Glutamic acid (E) at position 515 of the phi29 DNA polymerase to other amino acid residues.

Specifically, the point mutation A is the mutation of amino acid residue Methionine (M) at position 97 of the phi29 DNA polymerase to Histidine (H), Alanine (A) or Lysine (K); the point mutation B is the mutation of amino acid residue Leucine (L) at position 123 of the phi29 DNA polymerase to Lysine (K), Phenylalanine (F), Isoleucine (I) or Histidine (H); and the point mutation C is the mutation of amino acid residue Glutamic acid (E) at position 515 of the phi29 DNA polymerase to Glycine (G) or Proline (P).

Specifically, the protein is any one selected from protein (1) to (19):

(1) a protein obtained by subjecting the phi29 DNA polymerase to three point mutations and keeping remaining amino acids unchanged, wherein the three point mutations are the mutation of amino acid residue Methionine (M) at position 97 to Alanine (A), the mutation of amino acid residue Leucine (L) at position 123 to Histidine (H) and the mutation of amino acid residue Glutamic acid (E) at position 515 to Proline (P);

(2) a protein obtained by subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Isoleucine (I) and the mutation of amino acid residue Glutamic acid (E) at position 515 to Proline (P);

(3) a protein obtained by subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Phenylalanine (F) and the mutation of amino acid residue Glutamic acid (E) at position 515 to Proline (P);

(4) a protein obtained by subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Histidine (H) and the mutation of amino acid residue Glutamic acid (E) at position 515 to Proline (P);

(5) a protein obtained by subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Lysine (K) and the mutation of amino acid residue Glutamic acid (E) at position 515 to Proline (P);

(6) a protein obtained by subjecting the phi29 DNA polymerase to three point mutations and keeping remaining amino acids unchanged, wherein the three point mutations are the mutation of amino acid residue Methionine (M) at position 97 to Alanine (A), the mutation of amino acid residue Leucine (L) at position 123 to Phenylalanine (F) and the mutation of amino acid residue Glutamic acid (E) at position 515 to Glycine (G);

(7) a protein obtained by subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Histidine (H) and the mutation of amino acid residue Glutamic acid (E) at position 515 to Glycine (G);

(8) a protein obtained by subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Isoleucine (I) and the mutation of amino acid residue Glutamic acid (E) at position 515 to Glycine (G);

(9) a protein obtained by subjecting the phi29 DNA polymerase to three point mutations and keeping remaining amino acids unchanged, wherein the three point mutations are the mutation of amino acid residue Methionine (M) at position 97 to Alanine (A), the mutation of amino acid residue Leucine (L) at position 123 to Histidine (H) and the mutation of amino acid residue Glutamic acid (E) at position 515 to Glycine (G);

(10) a protein obtained by subjecting the phi29 DNA polymerase to three point mutations and keeping remaining amino acids unchanged, wherein the three point mutations are the mutation of amino acid residue Methionine (M) at position 97 to Histidine (H), the mutation of amino acid residue Leucine (L) at position 123 to Isoleucine (I) and the mutation of amino acid residue Glutamic acid (E) at position 515 to Glycine (G);

(11) a protein obtained by subjecting the phi29 DNA polymerase to three point mutations and keeping remaining amino acids unchanged, wherein the three point mutations are the mutation of amino acid residue Methionine (M) at position 97 to Histidine (H), the mutation of amino acid residue Leucine (L) at position 123 to Histidine (H) and the mutation of amino acid residue Glutamic acid (E) at position 515 to Glycine (G);

(12) a protein obtained by subjecting the phi29 DNA polymerase to two point mutations and keeping remaining amino acids unchanged, wherein the two point mutations are the mutation of amino acid residue Methionine (M) at position 97 to Alanine (A) and the mutation of amino acid residue Leucine (L) at position 123 to Isoleucine (I);

(13) a protein obtained by subjecting the phi29 DNA polymerase to two point mutations and keeping remaining amino acids unchanged, wherein the two point mutations are the mutation of amino acid residue Methionine (M) at position 97 to Histidine (H) and the mutation of amino acid residue Glutamic acid (E) at position 515 to Glycine (G);

(14) a protein obtained by subjecting the phi29 DNA polymerase to two point mutations and keeping remaining amino acids unchanged, wherein the two point mutations are the mutation of amino acid residue Methionine (M) at position 97 to Lysine (K) and the mutation of amino acid residue Glutamic acid (E) at position 515 to Glycine (G);

(15) a protein obtained by subjecting the phi29 DNA polymerase to one point mutation and keeping remaining amino acids unchanged, wherein the one point mutation is the mutation of amino acid residue Methionine (M) at position 97 to Alanine (A);

(16) a protein obtained by subjecting the phi29 DNA polymerase to one point mutation and keeping remaining amino acids unchanged, wherein the one point mutation is the mutation of amino acid residue Methionine (M) at position 97 to Lysine (K);

(17) a protein obtained by subjecting the phi29 DNA polymerase to one point mutation and keeping remaining amino acids unchanged, wherein the one point mutation is the mutation of amino acid residue Leucine (L) at position 123 to Lysine (K);

(18) a protein obtained by subjecting the phi29 DNA polymerase to one point mutation and keeping remaining amino acids unchanged, wherein the one point mutation is the mutation of amino acid residue Glutamic acid (E) at position 515 to Glycine (G); and

(19) a fusion protein obtained by ligating a tag at the N-terminus and/or the C-terminus of any protein of (1) to (18).

Specifically, the protein may be a fusion protein obtained by ligating a $His_6$ tag at terminus of any protein of (1) to (18). More specifically, the protein may be a fusion protein obtained by ligating a $His_6$ tag at the N-terminus of any protein of (1) to (18).

The protein as described above has increased stability compared to the phi29 DNA polymerase. Specifically, the stability is thermal stability. More specifically, the thermal stability may be a thermal stability at 37° C.

The present disclosure in embodiments also provides a nucleic acid molecule encoding the protein as described above, an expression cassette containing the nucleic acid molecule, a recombinant vector containing the nucleic acid molecule, a recombinant bacterium containing the nucleic acid molecule, and a transgenic cell line containing the nucleic acid molecule.

Specifically, the nucleic acid molecule may be any DNA molecule of (1) to (19):

(1) a DNA molecule obtained by mutating the nucleotides "ATG" at positions 289-291 to "GCG", the nucleotides "CTG" at positions 367-369 to "CAT" and the nucleotides "GAA" at positions 1543-1545 to "CCG", relative to the DNA molecule shown in SEQ ID NO: 2 in the sequence listing;

(2) a DNA molecule obtained by mutating the nucleotides "ATG" at positions 289-291 to "AAA", the nucleotides "CTG" at positions 367-369 to "ATT" and the nucleotides "GAA" at positions 1543-1545 to "CCG", relative to the DNA molecule shown in SEQ ID NO: 2 in the sequence listing;

(3) a DNA molecule obtained by mutating the nucleotides "ATG" at positions 289-291 to "AAA", the nucleotides "CTG" at positions 367-369 to "TTT" and the nucleotides "GAA" at positions 1543-1545 to "CCG", relative to the DNA molecule shown in SEQ ID NO: 2 in the sequence listing;

(4) a DNA molecule obtained by mutating the nucleotides "ATG" at positions 289-291 to "AAA", the nucleotides "CTG" at positions 367-369 to "CAT" and the nucleotides "GAA" at positions 1543-1545 to "CCG", relative to the DNA molecule shown in SEQ ID NO: 2 in the sequence listing;

(5) a DNA molecule obtained by mutating the nucleotides "ATG" at positions 289-291 to "AAA", the nucleotides "CTG" at positions 367-369 to "AAA" and the nucleotides "GAA" at positions 1543-1545 to "CCG", relative to the DNA molecule shown in SEQ ID NO: 2 in the sequence listing;

(6) a DNA molecule obtained by mutating the nucleotides "ATG" at positions 289-291 to "GCG", the nucleotides "CTG" at positions 367-369 to "TTT" and the nucleotides "GAA" at positions 1543-1545 to "GGC", relative to the DNA molecule shown in SEQ ID NO: 2 in the sequence listing;

(7) a DNA molecule obtained by mutating the nucleotides "ATG" at positions 289-291 to "AAA", the nucleotides "CTG" at positions 367-369 to "CAT" and the nucleotides "GAA" at positions 1543-1545 to "GGC", relative to the DNA molecule shown in SEQ ID NO: 2 in the sequence listing;

(8) a DNA molecule obtained by mutating the nucleotides "ATG" at positions 289-291 to "AAA", the nucleotides "CTG" at positions 367-369 to "ATT" and the nucleotides "GAA" at positions 1543-1545 to "GGC", relative to the DNA molecule shown in SEQ ID NO: 2 in the sequence listing;

(9) a DNA molecule obtained by mutating the nucleotides "ATG" at positions 289-291 to "GCG", the nucleotides "CTG" at positions 367-369 to "CAT" and the nucleotides "GAA" at positions 1543-1545 to "GGC", relative to the DNA molecule shown in SEQ ID NO: 2 in the sequence listing;

(10) a DNA molecule obtained by mutating the nucleotides "ATG" at positions 289-291 to "CAT", the nucleotides "CTG" at positions 367-369 to "ATT" and the nucleotides "GAA" at positions 1543-1545 to "GGC", relative to the DNA molecule shown in SEQ ID NO: 2 in the sequence listing;

(11) a DNA molecule obtained by mutating the nucleotides "ATG" at positions 289-291 to "CAT", the nucleotides "CTG" at positions 367-369 to "CAT" and the nucleotides "GAA" at positions 1543-1545 to "GGC", relative to the DNA molecule shown in SEQ ID NO: 2 in the sequence listing;

(12) a DNA molecule obtained by mutating the nucleotides "ATG" at positions 289-291 to "GCG" and the nucleotides "CTG" at positions 367-369 to "ATT", relative to the DNA molecule shown in SEQ ID NO: 2 in the sequence listing;

(13) a DNA molecule obtained by mutating the nucleotides "ATG" at positions 289-291 to "AAA" and the nucleotides "GAA" at positions 1543-1545 to "GGC", relative to the DNA molecule shown in SEQ ID NO: 2 in the sequence listing;

(14) a DNA molecule obtained by mutating the nucleotides "ATG" at positions 289-291 to "CAT" and the nucleotides "GAA" at positions 1543-1545 to "GGC", relative to the DNA molecule shown in SEQ ID NO: 2 in the sequence listing;

(15) a DNA molecule obtained by mutating the nucleotides "ATG" at positions 289-291 to "GCG" relative to the DNA molecule shown in SEQ ID NO: 2 in the sequence listing;

(16) a DNA molecule obtained by mutating the nucleotides "CTG" at positions 367-369 to "AAA" relative to the DNA molecule shown in SEQ ID NO: 2 in the sequence listing;

(17) a DNA molecule obtained by mutating the nucleotides "GAA" at positions 1543-1545 to "GGC" relative to the DNA molecule shown in SEQ ID NO: 2 in the sequence listing;

(18) a fusion DNA molecule obtained by ligating nucleotides encoding a tag at 5' end and/or 3'end of any DNA molecule of (1) to (17); and

(19) a DNA molecule having 90% or more sequence homology with the DNA molecule as defined in (1) to (18) and encoding the protein as described above.

The recombinant vector is obtained by inserting the nucleic acid molecule into an expression vector.

Specifically, the expression vector may be a pET28a (+) vector.

The recombinant bacterium is a bacterium obtained by introducing the recombinant vector into an original bacterium.

The original bacterium may be *Escherichia coli* (*E. coli*).

Specifically, the *Escherichia coli* may be *E. coli* BL21 (DE3).

The transgenic cell line may be obtained by transforming the recombinant vector into recipient cells. The transgenic cell line is a non-plant propagative material.

The present disclosure in embodiments further provides use of the protein as described above for any one of (a) to (g):

(a) as a DNA polymerase;
(b) catalyzing DNA replication and/or DNA amplification;
(c) catalyzing rolling circle amplification and/or multiple-strand displacement amplification;
(d) preparing a kit for catalyzing DNA replication and/or DNA amplification;
(e) preparing a kit for catalyzing rolling circle amplification and/or multiple-strand displacement amplification;
(f) DNA sequencing or RNA sequencing; and
(g) preparing a kit for DNA sequencing or RNA sequencing.

The present disclosure in embodiments further provides use of the nucleic acid molecule encoding the protein as described above, the expression cassette containing the nucleic acid molecule, the recombinant vector containing the nucleic acid molecule, the recombinant bacterium containing the nucleic acid molecule and the transgenic cell line containing the nucleic acid molecule, for any one of (h) to (k):

(h) preparing a DNA polymerase;
(i) preparing a kit for catalyzing DNA replication and/or DNA amplification;
(j) preparing a kit for catalyzing rolling circle amplification and/or multiple-strand displacement amplification; and
(k) preparing a kit for DNA sequencing or RNA sequencing.

The present disclosure in embodiments further provides a method of improving the stability of phi29 DNA polymerase, comprising subjecting a phi29 DNA polymerase shown in SEQ ID NO: 1 to point mutation A and/or point mutation B and/or point mutation C, wherein the point mutation A is the mutation of amino acid residue Methionine (M) at position 97 of the phi29 DNA polymerase to other amino acid residues; the point mutation B is the mutation of amino acid residue Leucine (L) at position 123 of the phi29 DNA polymerase to other amino acid residues; and the point mutation C is the mutation of amino acid residue Glutamic acid (E) at position 515 of the phi29 DNA polymerase to other amino acid residues.

Specifically, the point mutation A may be the mutation of amino acid residue Methionine (M) at position 97 of the phi29 DNA polymerase to Histidine (H), Alanine (A) or Lysine (K); the point mutation B may be the mutation of amino acid residue Leucine (L) at position 123 of the phi29 DNA polymerase to Lysine (K), Phenylalanine (F), Isoleucine (I) or Histidine (H); and the point mutation C may be the mutation of amino acid residue Glutamic acid (E) at position 515 of the phi29 DNA polymerase to Glycine (G) or Proline (P).

The method as described above may be any one of procedures (1) to (18):

(1) subjecting the phi29 DNA polymerase to three point mutations and keeping remaining amino acids unchanged, wherein the three point mutations are the mutation of amino acid residue Methionine (M) at position 97 to Alanine (A), the mutation of amino acid residue Leucine (L) at position 123 to Histidine (H) and the mutation of amino acid residue Glutamic acid (E) at position 515 to Proline (P);

(2) subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Isoleucine (I) and the mutation of amino acid residue Glutamic acid (E) at position 515 to Proline (P);

(3) subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Phenylalanine (F) and the mutation of amino acid residue Glutamic acid (E) at position 515 to Proline (P);

(4) subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Histidine (H) and the mutation of amino acid residue Glutamic acid (E) at position 515 to Proline (P);

(5) subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Lysine (K) and the mutation of amino acid residue Glutamic acid (E) at position 515 to Proline (P);

(6) subjecting the phi29 DNA polymerase to three point mutations and keeping remaining amino acids unchanged, wherein the three point mutations are the mutation of amino acid residue Methionine (M) at position 97 to Alanine (A), the mutation of amino acid residue Leucine (L) at position 123 to Phenylalanine (F) and the mutation of amino acid residue Glutamic acid (E) at position 515 to Glycine (G);

(7) subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Histidine (H) and the mutation of amino acid residue Glutamic acid (E) at position 515 to Glycine (G);

(8) subjecting the phi29 DNA polymerase to three point mutations and keeping remaining amino acids unchanged, wherein the three point mutations are the mutation of amino acid residue Methionine (M) at position 97 to Lysine (K), the mutation of amino acid residue Leucine (L) at position 123 to Isoleucine (I) and the mutation of amino acid residue Glutamic acid (E) at position 515 to Glycine (G);

(9) subjecting the phi29 DNA polymerase to three point mutations and keeping remaining amino acids unchanged, wherein the three point mutations are the mutation of amino acid residue Methionine (M) at position 97 to Alanine (A), the mutation of amino acid residue Leucine (L) at position 123 to Histidine (H) and the mutation of amino acid residue Glutamic acid (E) at position 515 to Glycine (G);

(10) subjecting the phi29 DNA polymerase to three point mutations and keeping remaining amino acids unchanged, wherein the three point mutations are the mutation of amino acid residue Methionine (M) at position 97 to Histidine (H), the mutation of amino acid residue Leucine (L) at position 123 to Isoleucine (I) and the mutation of amino acid residue Glutamic acid (E) at position 515 to Glycine (G);

(11) subjecting the phi29 DNA polymerase to three point mutations and keeping remaining amino acids unchanged, wherein the three point mutations are the mutation of amino acid residue Methionine (M) at position 97 to Histidine (H), the mutation of amino acid residue Leucine (L) at position 123 to Histidine (H) and the mutation of amino acid residue Glutamic acid (E) at position 515 to Glycine (G);

(12) subjecting the phi29 DNA polymerase to two point mutations and keeping remaining amino acids unchanged, wherein the two point mutations are the mutation of amino acid residue Methionine (M) at position 97 to Alanine (A) and the mutation of amino acid residue Leucine (L) at position 123 to Isoleucine (I);

(13) subjecting the phi29 DNA polymerase to two point mutations and keeping remaining amino acids unchanged, wherein the two point mutations are the mutation of amino acid residue Methionine (M) at position 97 to Histidine (H) and the mutation of amino acid residue Glutamic acid (E) at position 515 to Glycine (G);

(14) subjecting the phi29 DNA polymerase to two point mutations and keeping remaining amino acids unchanged, wherein the two point mutations are the mutation of amino acid residue Methionine (M) at position 97 to Lysine (K) and the mutation of amino acid residue Glutamic acid (E) at position 515 to Glycine (G);

(15) subjecting the phi29 DNA polymerase to one point mutation and keeping remaining amino acids unchanged, wherein the one point mutation is the mutation of amino acid residue Methionine (M) at position 97 to Alanine (A);

(16) subjecting the phi29 DNA polymerase to one point mutation and keeping remaining amino acids unchanged, wherein the one point mutation is the mutation of amino acid residue Methionine (M) at position 97 to Lysine (K);

(17) subjecting the phi29 DNA polymerase to one point mutation and keeping remaining amino acids unchanged, wherein the one point mutation is the mutation of amino acid residue Leucine (L) at position 123 to Lysine (K); and

(18) subjecting the phi29 DNA polymerase to one point mutation and keeping remaining amino acids unchanged, wherein the one point mutation is the mutation of amino acid residue Glutamic acid (E) at position 515 to Glycine (G).

Specifically, the stability may be thermal stability. More specifically, the thermal stability may be a thermal stability at 37° C.

Specifically, the phi29 DNA polymerase may be (I), (II) or (III):

(I) a protein shown in SEQ ID NO: 1 in the sequence listing;

(II) a protein having 90% or more homology with the sequence shown in SEQ ID NO: 1 in the sequence listing and derived from *Bacillus subtilis*; and (III) a protein having 95% or more homology with the sequence shown in SEQ ID NO: 1 in the sequence listing and derived from *Bacillus subtilis*.

DETAILED DESCRIPTION

The following examples are for better understanding of the present disclosure rather than limiting. Unless otherwise specified, the experimental methods in the following examples are conventional methods, and the test materials used in the following examples are purchased from conventional biochemical reagent companies. The quantitative experiments in the following examples are all set up in triplicate, with averaged results. Solvent in each solution or buffer solution in the following examples is water, unless otherwise specified.

pET28a (+) vector is from Novagen.

E. coli BL21 (DE3) is from TIANGEN, in a catalog number of CB105-02.

Storage buffer includes 10 mM Tris-HCl, 100 mM KCl, 1 mM DTT, 0.1 mM EDTA, 0.5% (v/v) Tween® 20, 0.5% (v/v) NP-40 and 50% (v/v) Glycerol, with pH7.4 @ 25° C.

141 RCA Primer in the examples is of a sequence: TCCTAAGACCGCTTGGCCTCCGACT (SEQ ID NO: 3).

141Ad ssDNA in the examples is generated by BGI and is a circular single-strand library in a certain size range, without fixed sequences. Specifically, it is a random library consisting of four nucleotides (A/T/C/G), with a main band in a length of 200 to 300 bp.

Example 1 Construction of Recombinant Bacterium and Purification of Protein 1.1 Construction of Recombinant Vector A wild-type recombinant vector (recombinant vector WT) was obtained by inserting the DNA molecule as shown in SEQ ID NO: 2 in the sequence listing between the NdeI and BamHI restriction sites of pET28a (+) vector. The DNA molecule as shown in SEQ ID NO: 2 in the sequence listing expresses the protein as shown in SEQ ID NO: 1 in the sequence listing, that is, the wild-type phi29 DNA polymerase represented by WT.

Different recombinant vectors were obtained by subjecting the recombinant vector WT as the original vector to point mutations in the presence of respective primer pairs in Table 1.

TABLE 1

| Point mutation | Forward primer | Reverse primer |
| --- | --- | --- |
| 97H | CACCATTATTAGCCGCCATGGCCAGTGGTATATGATTG (SEQ ID NO: 4) | CAATCATATACCACTGGCCATGGCGGCTAATAATGGTG (SEQ ID NO: 5) |
| 97A | CACCATTATTAGCCGCGCGGGCCAGTGGTATATGATTG (SEQ ID NO: 6) | CAATCATATACCACTGGCCCGCGCGGCTAATAATGGTG (SEQ ID NO: 7) |
| 97K | CACCATTATTAGCCGCAAAGGCCAGTGGTATATGATTG (SEQ ID NO: 8) | CAATCATATACCACTGGCCTTTGCGGCTAATAATGGTG (SEQ ID NO: 9) |

TABLE 1-continued

| Point mutation | Forward primer | Reverse primer |
| --- | --- | --- |
| 123K | CCGTGATCTATGATAGCAAAAAGAAACTGCCGTTTCCG (SEQ ID NO: 10) | CGGAAACGGCAGTTTCTTTTTGCTATCATAGATCACGG (SEQ ID NO: 11) |
| 123F | CCGTGATCTATGATAGCTTTAAGAAACTGCCGTTTCCG (SEQ ID NO: 12) | CGGAAACGGCAGTTTCTTAAAGCTATCATAGATCACGG (SEQ ID NO: 13) |
| 123I | CCGTGATCTATGATAGCATTAAGAAACTGCCGTTTCCG (SEQ ID NO: 14) | CGGAAACGGCAGTTTCTTAATGCTATCATAGATCACGG (SEQ ID NO: 15) |
| 123H | CCGTGATCTATGATAGCCATAAGAAACTGCCGTTTCCG (SEQ ID NO: 16) | CGGAAACGGCAGTTTCTTATGGCTATCATAGATCACGG (SEQ ID NO: 17) |
| 515P | GGATGGCAAACTGGTTCCGGGCAGCCCGGATG (SEQ ID NO: 18) | CATCCGGGCTGCCCGGAACCAGTTTGCCAT CC (SEQ ID NO: 19) |
| 515G | GGATGGCAAACTGGTTGGCGGCAGCCCGGATG (SEQ ID NO: 20) | CATCCGGGCTGCCGCCAACCAGTTTGCCAT CC (SEQ ID NO: 21) |

The recombinant vector M97A differs with the recombinant vector WT only in that the nucleotides 289-291 of the DNA molecule shown in SEQ ID NO: 2 in the sequence listing are mutated from "ATG" to "GCG", with mutated DNA molecule encoding mutant M97A. The mutant M97A differs with the wild-type phi29 DNA polymerase only in that the amino acid residue at position 97 is mutated from Methionine (M) to Alanine (A).

The recombinant vector M97K differs with the recombinant vector WT only in that the nucleotides 289-291 of the DNA molecule shown in SEQ ID NO: 2 in the sequence listing are mutated from "ATG" to "AAA", with mutated DNA molecule encoding mutant M97K. The mutant M97K differs with the wild-type phi29 DNA polymerase only in that the amino acid residue at position 97 is mutated from Methionine (M) to Lysine (K).

The recombinant vector L123K differs with the recombinant vector WT only in that the nucleotides 367-369 of the DNA molecule shown in SEQ ID NO: 2 in the sequence listing are mutated from "CTG" to "AAA", with mutated DNA molecule encoding mutant L123K. The mutant L123K differs with the wild-type phi29 DNA polymerase only in that the amino acid residue at position 123 is mutated from Leucine (L) to Lysine (K).

The recombinant vector E515G differs with the recombinant vector WT only in that the nucleotides 1543-1545 of the DNA molecule shown in SEQ ID NO: 2 in the sequence listing are mutated from "GAA" to "GGC", with mutated DNA molecule encoding mutant E515G. The mutant E515G differs with the wild-type phi29 DNA polymerase only in that the amino acid residue at position 515 is mutated from Glutamic acid (E) to Glycine (G).

The recombinant vector M97A-L123I differs with the recombinant vector WT only in that the nucleotides 289-291 are mutated from "ATG" to "GCG" and the nucleotides 367-369 are mutated from "CTG" to "ATT" respective to the DNA molecule shown in SEQ ID NO: 2 in the sequence listing, with mutated DNA molecule encoding mutant M97A-L123I. The mutant M97A-L123I differs with the wild-type phi29 DNA polymerase only in that the amino acid residue at position 97 is mutated from Methionine (M) to Alanine (A) and the amino acid residue at position 123 is mutated from Leucine (L) to Isoleucine (I).

The recombinant vector M97A-L123H-E515G differs with the recombinant vector WT only in that the nucleotides 289-291 are mutated from "ATG" to "GCG", the nucleotides 367-369 are mutated from "CTG" to "CAT" and the nucleotides 1543-1545 are mutated from "GAA" to "GGC" respective to the DNA molecule shown in SEQ ID NO: 2 in the sequence listing, with mutated DNA molecule encoding mutant M97A-L123H-E515G. The mutant M97A-L123H-E515G differs with the wild-type phi29 DNA polymerase only in that the amino acid residue at position 97 is mutated from Methionine (M) to Alanine (A), the amino acid residue at position 123 is mutated from Leucine (L) to Histidine (H) and the amino acid residue at position 515 is mutated from Glutamic acid (E) to Glycine (G).

The recombinant vector M97A-L123F-E515G differs with the recombinant vector WT only in that the nucleotides 289-291 are mutated from "ATG" to "GCG", the nucleotides 367-369 are mutated from "CTG" to "TTT" and the nucleotides 1543-1545 are mutated from "GAA" to "GGC" respective to the DNA molecule shown in SEQ ID NO: 2 in the sequence listing, with mutated DNA molecule encoding mutant M97A-L123F-E515G. The mutant M97A-L123F-E515G differs with the wild-type phi29 DNA polymerase only in that the amino acid residue at position 97 is mutated from Methionine (M) to Alanine (A), the amino acid residue at position 123 is mutated from Leucine (L) to Phenylalanine (F) and the amino acid residue at position 515 is mutated from Glutamic acid (E) to Glycine (G).

The recombinant vector M97A-L123H-E515P differs with the recombinant vector WT only in that the nucleotides 289-291 are mutated from "ATG" to "GCG", the nucleotides 367-369 are mutated from "CTG" to "CAT" and the nucleotides 1543-1545 are mutated from "GAA" to "CCG" respective to the DNA molecule shown in SEQ ID NO: 2 in the sequence listing, with mutated DNA molecule encoding mutant M97A-L123H-E515P. The mutant M97A-L123H-E515P differs with the wild-type phi29 DNA polymerase only in that the amino acid residue at position 97 is mutated from Methionine (M) to Alanine (A), the amino acid residue at position 123 is mutated from Leucine (L) to Histidine (H) and the amino acid residue at position 515 is mutated from Glutamic acid (E) to Proline (P).

The recombinant vector M97K-E515G differs with the recombinant vector WT only in that the nucleotides 289-291 are mutated from "ATG" to "AAA" and the nucleotides 1543-1545 are mutated from "GAA" to "GGC" respective to the DNA molecule shown in SEQ ID NO: 2 in the sequence listing, with mutated DNA molecule encoding mutant M97K-E515G. The mutant M97K-E515G differs with the wild-type phi29 DNA polymerase only in that the amino acid residue at position 97 is mutated from Methionine (M) to Lysine (K) and the amino acid residue at position 515 is mutated from Glutamic acid (E) to Glycine (G).

The recombinant vector M97K-L123K-E515P differs with the recombinant vector WT only in that the nucleotides 289-291 are mutated from "ATG" to "AAA", the nucleotides 367-369 are mutated from "CTG" to "AAA" and the nucleotides 1543-1545 are mutated from "GAA" to "CCG" respective to the DNA molecule shown in SEQ ID NO: 2 in the sequence listing, with mutated DNA molecule encoding mutant M97K-L123K-E515P. The mutant M97K-L123K-E515P differs with the wild-type phi29 DNA polymerase only in that the amino acid residue at position 97 is mutated from Methionine (M) to Lysine (K), the amino acid residue at position 123 is mutated from Leucine (L) to Lysine (K) and the amino acid residue at position 515 is mutated from Glutamic acid (E) to Proline (P).

The recombinant vector M97K-L123F-E515P differs with the recombinant vector WT only in that the nucleotides 289-291 are mutated from "ATG" to "AAA", the nucleotides 367-369 are mutated from "CTG" to "TTT" and the nucleotides 1543-1545 are mutated from "GAA" to "CCG" respective to the DNA molecule shown in SEQ ID NO: 2 in the sequence listing, with mutated DNA molecule encoding mutant M97K-L123F-E515P. The mutant M97K-L123F-E515P differs with the wild-type phi29 DNA polymerase only in that the amino acid residue at position 97 is mutated from Methionine (M) to Lysine (K), the amino acid residue at position 123 is mutated from Leucine (L) to Phenylalanine (F) and the amino acid residue at position 515 is mutated from Glutamic acid (E) to Proline (P).

The recombinant vector M97K-L123I-E515G differs with the recombinant vector WT only in that the nucleotides 289-291 are mutated from "ATG" to "AAA", the nucleotides 367-369 are mutated from "CTG" to "ATT" and the nucleotides 1543-1545 are mutated from "GAA" to "GGC" respective to the DNA molecule shown in SEQ ID NO: 2 in the sequence listing, with mutated DNA molecule encoding mutant M97K-L123I-E515G. The mutant M97K-L123I-E515G differs with the wild-type phi29 DNA polymerase only in that the amino acid residue at position 97 is mutated from Methionine (M) to Lysine (K), the amino acid residue at position 123 is mutated from Leucine (L) to Isoleucine (I) and the amino acid residue at position 515 is mutated from Glutamic acid (E) to Glycine (G).

The recombinant vector M97K-L123H-E515G differs with the recombinant vector WT only in that the nucleotides 289-291 are mutated from "ATG" to "AAA", the nucleotides 367-369 are mutated from "CTG" to "CAT" and the nucleotides 1543-1545 are mutated from "GAA" to "GGC" respective to the DNA molecule shown in SEQ ID NO: 2 in the sequence listing, with mutated DNA molecule encoding mutant M97K-L123H-E515G. The mutant M97K-L123H-E515G differs with the wild-type phi29 DNA polymerase only in that the amino acid residue at position 97 is mutated from Methionine (M) to Lysine (K), the amino acid residue at position 123 is mutated from Leucine (L) to Histidine (H) and the amino acid residue at position 515 is mutated from Glutamic acid (E) to Glycine (G).

The recombinant vector M97K-L123I-E515P differs with the recombinant vector WT only in that the nucleotides 289-291 are mutated from "ATG" to "AAA", the nucleotides 367-369 are mutated from "CTG" to "ATT" and the nucleotides 1543-1545 are mutated from "GAA" to "CCG" respective to the DNA molecule shown in SEQ ID NO: 2 in the sequence listing, with mutated DNA molecule encoding mutant M97K-L123I-E515P. The mutant M97K-L123I-E515P differs with the wild-type phi29 DNA polymerase only in that the amino acid residue at position 97 is mutated from Methionine (M) to Lysine (K), the amino acid residue at position 123 is mutated from Leucine (L) to Isoleucine (I) and the amino acid residue at position 515 is mutated from Glutamic acid (E) to Proline (P).

The recombinant vector M97K-L123H-E515P differs with the recombinant vector WT only in that the nucleotides 289-291 are mutated from "ATG" to "AAA", the nucleotides 367-369 are mutated from "CTG" to "CAT" and the nucleotides 1543-1545 are mutated from "GAA" to "CCG" respective to the DNA molecule shown in SEQ ID NO: 2 in the sequence listing, with mutated DNA molecule encoding mutant M97K-L123H-E515P. The mutant M97K-L123H-E515P differs with the wild-type phi29 DNA polymerase only in that the amino acid residue at position 97 is mutated from Methionine (M) to Lysine (K), the amino acid residue at position 123 is mutated from Leucine (L) to Histidine (H) and the amino acid residue at position 515 is mutated from Glutamic acid (E) to Proline (P).

The recombinant vector M97H-E515G differs with the recombinant vector WT only in that the nucleotides 289-291 are mutated from "ATG" to "CAT" and the nucleotides 1543-1545 are mutated from "GAA" to "GGC" respective to the DNA molecule shown in SEQ ID NO: 2 in the sequence listing, with mutated DNA molecule encoding mutant M97H-E515G. The mutant M97H-E515G differs with the wild-type phi29 DNA polymerase only in that the amino acid residue at position 97 is mutated from Methionine (M) to Histidine (H) and the amino acid residue at position 515 is mutated from Glutamic acid (E) to Glycine (G).

The recombinant vector M97H-L123I-E515G differs with the recombinant vector WT only in that the nucleotides 289-291 are mutated from "ATG" to "CAT", the nucleotides 367-369 are mutated from "CTG" to "ATT" and the nucleotides 1543-1545 are mutated from "GAA" to "GGC" respective to the DNA molecule shown in SEQ ID NO: 2 in the sequence listing, with mutated DNA molecule encoding mutant M97H-L123I-E515G. The mutant M97H-L123I-E515G differs with the wild-type phi29 DNA polymerase only in that the amino acid residue at position 97 is mutated from Methionine (M) to Histidine (H), the amino acid residue at position 123 is mutated from Leucine (L) to Isoleucine (I) and the amino acid residue at position 515 is mutated from Glutamic acid (E) to Glycine (G).

The recombinant vector M97H-L123H-E515G differs with the recombinant vector WT only in that the nucleotides 289-291 are mutated from "ATG" to "CAT", the nucleotides 367-369 are mutated from "CTG" to "CAT" and the nucleotides 1543-1545 are mutated from "GAA" to "GGC" respective to the DNA molecule shown in SEQ ID NO: 2 in the sequence listing, with mutated DNA molecule encoding mutant M97H-L123H-E515G. The mutant M97H-L123H-E515G differs with the wild-type phi29 DNA polymerase only in that the amino acid residue at position 97 is mutated from Methionine (M) to Histidine (H), the amino acid residue at position 123 is mutated from Leucine (L) to Histidine (H) and the amino acid residue at position 515 is mutated from Glutamic acid (E) to Glycine (G).

1.2 Construction of Recombinant Bacterium

Different recombinant bacterium was obtained by introducing respective recombinant vector constructed in step 1.1 into *E. coli* BL21 (DE3).

Recombinant bacteria obtained were respectively named as recombinant bacterium WT, recombinant bacterium M97A, recombinant bacterium L123K, recombinant bacterium E515G, recombinant bacterium M97A-L123I, recombinant bacterium M97A-L123H-E515G, recombinant bacterium M97A-L123F-E515G, recombinant bacterium M97A-L123H-E515P, recombinant bacterium M97K-E515G, recombinant bacterium M97K-L123K-E515P, recombinant bacterium M97K-L123F-E515P, recombinant bacterium M97K-L123I-E515G, recombinant bacterium M97K-L123H-E515G, recombinant bacterium M97K-L123I-E515P, recombinant bacterium M97K-L123H-E515P, recombinant bacterium M97H-E515G, recombinant bacterium M97H-L123I-E515G and recombinant bacterium M97H-L123H-E515G, according to the principle corresponding to the name of recombinant vector.

1.3 Induced Expression of Recombinant Bacterium

The recombinant bacteria obtained in step 1.2 were respectively subjected to induction and purification, thus obtaining proteins fused to $His_6$ tag at N-terminus. Such proteins obtained were respectively named as a wild-type phi29 DNA polymerase with $His_6$ tag, a mutant M97A with $His_6$ tag, a mutant L123K with $His_6$ tag, a mutant E515G with $His_6$ tag, a mutant M97A-L123I with $His_6$ tag, a mutant M97A-L123H-E515G with $His_6$ tag, a mutant M97A-L123F-E515G with $His_6$ tag, a mutant M97A-L123H-E515P with $His_6$ tag, a mutant M97K-E515G with $His_6$ tag, a mutant M97K-L123K-E515P with $His_6$ tag, a mutant M97K-L123F-E515P with $His_6$ tag, a mutant M97K-L123I-E515G with $His_6$ tag, a mutant M97K-L123H-E515G with $His_6$ tag, a mutant M97K-L123I-E515P with $His_6$ tag, a mutant M97K-L123H-E515P with $His_6$ tag, a mutant M97H-E515G with $His_6$ tag, a mutant M97H-L123I-E515G with $His_6$ tag and a mutant M97H-L123H-E515G with $His_6$ tag, according to the principle corresponding to the name of recombinant bacterium.

1.3.1 the Induction Process was Conducted Through the Following Specific Steps:

1.3.1.1 Activation of Bacterium

The recombinant bacteria were inoculated into 3 ml liquid LB medium containing kanamycin, followed by culturing overnight.

1.3.1.2 Transfer of Bacterium Solution

After the step 1.3.1.1, the obtained bacterium solution was transferred into 2 ml liquid LB medium containing kanamycin in volume of 1:100, followed by culturing under shaking at 37° C. and 220 rpm to reach an $OD_{600\ nm}$ value of 0.6, in which the $OD_{600\ nm}$ value in a range of 0.4 to 0.8 is suitable in practice.

1.3.1.3 Induction Process

After the step 1.3.1.2, isopropyl-β-D-thiogalactoside (IPTG) was added to the system to be a final concentration of 0.5 mM, followed by culturing under shaking at 16° C. and 220 rpm for 12 hours.

1.3.1.4 Collection of Bacterial Cells

After the step 1.3.1.3, the system was centrifuged at 4° C. and 8000 rpm for 5 minutes to collect bacterial cells.

1.3.2 Bacterial cells were purified by using ÄKTA Pure purification system from GE through the following specific steps.

1.3.2.1 The bacterial cells obtained in step 1.3.1 were shakily mixed with the suspension buffer (20 mM Tris-HCl, 500 mM NaCl, 20 mM Imidazole, 5% Glycerol; pH 7.9 @ 25° C.), ultrasonicated on ice, and centrifuged at 4° C. and 12,000 rpm for 30 minutes, thus collecting the supernatant.

1.3.2.2 The supernatant obtained in 1.3.2.1 was purified by using nickel column affinity chromatography (HisTrap FF 5 ml prepacked column). Specifically, the supernatant was loaded after the column was balanced by 10 column volumes of Buffer A, after which the column was washed with 20 column volumes of Buffer A and eluted with 15 column volumes of eluent consisting of Buffer A and Buffer B, and the eluted solution with target protein was collected. During the elution, the volume fraction of Buffer B increased from 0% to 100% linearly, and the volume fraction of corresponding Buffer A decreased from 100% to 0% linearly.

Buffer A: 20 mM Tris-HCl, 500 mM NaCl, 20 mM Imidazole, 5% (v/v) Glycerol; pH 7.9@25° C.

Buffer B: 20 mM Tris-HCl, 500 mM NaCl, 500 mM Imidazole, 5% (v/v) Glycerol; pH 7.9@25° C.

1.3.2.3 The eluted solution obtained in 1.3.2.2 was purified by using strong anion column chromatography (HiTrap Q HP 5 ml prepacked column). Specifically, the eluted solution was loaded after the column was balanced by 10 column volumes of buffer mixture consisting of 59 volume % of Buffer A and 41 volume % of Buffer B. Collection of effluent was started after the protein peak occurred (that is, the UV detection value reached to be 20 mAu), and was stopped until the UV detection value dropped to 50 mAu again.

Buffer A: 20 mM Tris-HCl, 150 mM NaCl, 5% (v/v) Glycerol, pH 7.5@25° C.

Buffer B: 20 mM Tris-HCl, 1 M NaCl, 5% (v/v) Glycerol, pH 7.5@25° C.

1.3.2.4 The effluent obtained in 1.3.2.3 was purified by using cation exchange chromatography (HiTrap SP HP prepacked column), thus obtaining a protein sample solution with a purity greater than 95%. Specifically, the effluent was loaded after the column was balanced by 10 column volumes of Buffer A, after which the column was washed with 15 column volumes of Buffer A and eluted with 10 column volumes of eluent consisting of Buffer A and Buffer B. During the elution, the volume fraction of Buffer B increased from 0% to 50% linearly, and the volume fraction of corresponding Buffer A decreased from 100% to 50% linearly. Collection of effluent containing target protein was started after the UV detection value reached to be 50 mAu and was stopped until the UV detection value dropped to 100 mAu again.

Buffer A: 20 mM Tris-HCl, 150 mM NaCl, 5% (v/v) Glycerol, pH 7.5@25° C.

Buffer B: 20 mM Tris-HCl, 1 M NaCl, 5% (v/v) Glycerol, pH 7.5@25° C.

1.3.2.5 The target protein obtained in 1.3.2.4 was transferred to a dialysis bag, which was dialysed in the dialysis buffer overnight. The protein solution in the dialysis bag was collected and other components were added, thus obtaining a target protein solution containing 1 mg/ml of target protein. The other components in the target protein solution are 10 mM of Tris-HCl (pH7.4 @ 25° C.), 100 mM KCl, 1 mM DTT, 0.1 mM EDTA, 0.5% (v/v) NP-40, 0.5% (v/v) Tween20 and 50% (v/v) Glycerol.

Dialysis buffer: 23.75 mM Tris-HCl (pH 7.4@25° C.), 237.5 mM KCl, 2.375 mM DTT, 0.2375 mM EDTA and 5% (v/v) Glycerol.

Example 2 Enzyme Activity Test of Wild-Type Phi29 DNA Polymerase and Mutants

The taken target protein solution prepared in Example 1 (as an enzyme solution to be tested) was diluted to 5000 times by volume with the storage buffer, thoroughly mixed by a vortex shaker, and then stilled on ice for 5 minutes to obtain the solution to be tested.

2.1 A pre-reaction system in a PCR tube after mixing was subjected to procedures in a PCR instrument: 95° C. for 1 minute, 65° C. for 1 minute and 40° C. for 1 minute, with the hot lid set as a temperature of 102° C.

Pre-reaction system (80.8 µl): 50 mM Tris-HCl (pH 7.5), 4 mM DTT, 10 mM (NH$_4$)$_2$SO$_4$, 10 mM MgCl$_2$, 50 nM dNTP Mixture, 2 pM 141 RCA Primer and 18 ng 141Ad ssDNA.

2.2 After the step 2.1, the PCR tube was placed on ice when the temperature dropped to 4° C. For a test group, 1 µl of the solution to be tested was added; and for a negative control group, 1 µl of storage buffer was added. Both groups were mixed under shaking with a vortex shaker, centrifuged in a centrifuge for 5 seconds and then subjected to a procedure (i.e. heating at 30° C. for 60 minutes) in the PCR instrument, with the hot lid set as a temperature of 65° C.

2.3 After the step 2.2, 5 µl of 0.5M EDTA solution was added to terminate the reaction, and then mixed under shaking.

2.4 The activity of the mixture obtained in 2.3 was assayed with Qubit ssDNA Assay Kit (Q10212, INVITROGEN) according to the instructions, and the concentration of DNA Nano ball (DNB) in the reaction product was detected by using Qubit fluorometer 3.0.

Enzyme activity of enzyme solution to be tested=$\Delta DNB \times 5000 \div 37.38$ Note: ΔDNB is the difference of average concentration of reaction products in the reaction-terminated system between the test group and the negative control group, 5000 represents the dilution ratio and 37.38 represents the slope of function between enzyme activity and ΔDNB.

The results of enzyme activity of enzyme solution to be tested are shown in Table 2.

TABLE 2

| Polymerase | Average concentration of control group | Average concentration of test group | ΔDNB (ng/µl) | Enzyme activity (U/µl) |
|---|---|---|---|---|
| WT | 0.42 | 1.23 | 0.81 | 108 |
| E515G | 0.40 | 0.76 | 0.37 | 49.2 |
| L123K | 0.40 | 0.8 | 0.4 | 53.8 |
| M97A | 0.40 | 0.77 | 0.38 | 50.5 |

Example 3 Thermal Stability Test of Wild-Type Phi29 DNA Polymerase and Mutants

The taken target protein solution prepared in Example 1 was divided into two parts, which were respectively treated as follows.

First part: the target protein solution was placed in a metal bath preheated to 37° C. for 10 minutes and centrifuged at 4° C. and 13000 rpm for 1 minute to collect the supernatant. The supernatant obtained was diluted to 1000 times by volume with the storage buffer, thoroughly mixed by a vortex shaker, and then stilled on ice for 5 minutes to obtain the solution 1 to be tested.

Second part: the target protein solution was diluted to 5000 times by volume with the storage buffer, thoroughly mixed by a vortex shaker, and then stilled on ice for 5 minutes to obtain the solution 2 to be tested.

The solution 1 to be tested and the solution 2 to be tested were respectively detected according to steps 2.1 to 2.4 in Example 2.

Enzyme activity without heat treatment ($U1$)=$\Delta DNB \times 5000 \div 37.38$ in which, ΔDNB is the difference of average concentration of reaction products in the reaction-terminated system between the test group (second part) and the negative control group;

Enzyme activity with heat treatment ($U2$)=$\Delta DNB \times 1000 \div 37.38$ in which, ΔDNB is the difference of average concentration of reaction products in the reaction-terminated system between the test group (first part) and the negative control group;

5000 and 1000 represent the dilution ratio respectively, and 37.38 represents the slope of function between enzyme activity and ΔDNB; and Loss ratio of enzyme activity (%)=$(U1-U2) \div U1 \times 100\%$.

The results are shown in Table 3.

TABLE 3

| Mutant Nos | | | DNB (ng/μl) | ΔDNB (ng/μl) | Enzyme activity (U/μl) | Loss ratio of enzyme activity (%) |
|---|---|---|---|---|---|---|
| NO.1 | WT | without heat treatment | 1.23 | 0.81 | 108.45 | 100.0 |
| | | heat treatment | 0.41 | 0.00 | 0.00 | |
| | | negative control | 0.42 | | | |
| NO.2 | M97A-L123I | without heat treatment | 1.36 | 1.01 | 134.44 | 95.2 |
| | | heat treatment | 0.60 | 0.24 | 6.47 | |
| | | negative control | 0.36 | | | |
| NO.3 | M97A-L123H-E515G | without heat treatment | 0.74 | 0.32 | 42.78 | 59.2 |
| | | heat treatment | 1.07 | 0.65 | 17.47 | |
| | | negative control | 0.42 | | | |
| NO.4 | M97A-L123F-E515G | without heat treatment | 0.90 | 0.39 | 51.62 | 61.2 |
| | | heat treatment | 1.26 | 0.75 | 20.03 | |
| | | negative control | 0.51 | | | |
| NO.5 | M97A-L123H-E515P | without heat treatment | 0.91 | 0.40 | 53.55 | 26.0 |
| | | heat treatment | 1.99 | 1.48 | 39.61 | |
| | | negative control | 0.51 | | | |
| NO.6 | M97K-L123I-E515P | without heat treatment | 1.07 | 0.63 | 84.27 | 42.5 |
| | | heat treatment | 1.59 | 1.81 | 48.48 | |
| | | negative control | 0.44 | | | |
| NO.7 | M97K-L123H-E515P | without heat treatment | 0.90 | 0.45 | 60.84 | 35.2 |
| | | heat treatment | 1.92 | 1.47 | 39.43 | |
| | | negative control | 0.44 | | | |
| NO.8 | M97H-E515G | without heat treatment | 0.77 | 0.35 | 47.26 | 85.6 |
| | | heat treatment | 0.67 | 0.25 | 6.78 | |
| | | negative control | 0.42 | | | |
| NO.9 | M97H-L123I-E515G | without heat treatment | 0.87 | 0.46 | 60.91 | 86 |
| | | heat treatment | 0.74 | 0.32 | 8.53 | |
| | | negative control | 0.42 | | | |
| NO.10 | M97H-L123H-E515G | without heat treatment | 0.78 | 0.37 | 49.02 | 80.3 |
| | | heat treatment | 0.78 | 0.36 | 9.66 | |
| | | negative control | 0.42 | | | |
| NO.11 | M97A | without heat treatment | 0.77 | 0.38 | 50.52 | 92.6 |
| | | heat treatment | 0.53 | 0.14 | 3.72 | |
| | | negative control | 0.40 | | | |

TABLE 3-continued

| Mutant Nos | | | DNB (ng/μl) | ΔDNB (ng/μl) | Enzyme activity (U/μl) | Loss ratio of enzyme activity (%) |
|---|---|---|---|---|---|---|
| NO.12 | L123K | without heat treatment | 0.80 | 0.40 | 53.85 | 96.8 |
| | | heat treatment | 0.46 | 0.06 | 1.70 | |
| | | negative control | 0.40 | | | |
| NO.13 | E515G | without heat treatment | 0.76 | 0.37 | 49.28 | 87.4 |
| | | heat treatment | 0.63 | 0.23 | 6.23 | |
| | | negative control | 0.40 | | | |
| NO.14 | M97K | without heat treatment | 1.48 | 1.07 | 142.63 | 97.5 |
| | | heat treatment | 0.54 | 0.13 | 3.55 | |
| | | negative control | 0.41 | | | |
| NO.15 | M97K-E515G | without heat treatment | 1.32 | 0.92 | 123.40 | 94.67 |
| | | heat treatment | 0.65 | 0.25 | 6.58 | |
| | | negative control | 0.40 | | | |
| NO.16 | M97K-L123K-E515P | without heat treatment | 0.85 | 0.43 | 57.60 | 58.77 |
| | | heat treatment | 1.31 | 0.89 | 23.75 | |
| | | negative control | 0.42 | | | |
| NO.17 | M97K-L123F-E515P | without heat treatment | 0.86 | 0.45 | 60.80 | 53.03 |
| | | heat treatment | 1.48 | 1.07 | 28.56 | |
| | | negative control | 0.41 | | | |
| NO.18 | M97K-L123I-E515G | without heat treatment | 1.38 | 0.95 | 127.54 | 86.28 |
| | | heat treatment | 1.08 | 0.65 | 17.50 | |
| | | negative control | 0.43 | | | |
| NO.19 | M97K-L123H-E515G | without heat treatment | 1.45 | 1.05 | 140.41 | 85.80 |
| | | heat treatment | 1.15 | 0.75 | 19.94 | |
| | | negative control | 0.40 | | | |

Example 4 Effect of Wild-Type Phi29 DNA Polymerase and Mutants in DNA Sequencing Based on Example 3, several mutants with improved thermal stability were selected and detected for their effect on DNA sequencing through machine test on BGISEQ-500 sequencer according to the standard of BGISEQ-500 sequencer. All reagents used for the test are a complete set of PE50 V2.0 kit produced by BGI, *E. coli* Ad153 standard library produced by BGI and Qubit ssDNA Assay reagent produced by Invitrogen. The reagents used below are all included in the PE50 V2.0 kit, except for the library and Qubit ssDNA Assay reagent. The PE50 V2.0 reagent tank as described below only refers to the reagents used in the on-machine test.

4.1 Preparation of DNB

DNBs were prepared before on-machine test.

The DNBs were prepared through the specific steps as below.

4.1.1 Each tube containing 20 μl DNB preparation buffer, 6 ng *E. coli* Ad153 standard library and molecular-grade water (for making up to a 40 μl system) after mixed via centrifugation was subjected to procedures in a PCR instrument: hot lid set as a temperature of 103° C.; 95° C. for 1 minute, 65° C. for 1 minute and 40° C. for 1 minute; holding at 4° C. forever. After that, the tube was stilled on ice.

4.1.2 After the step 4.1.1, 40 μl DNB polymerase mixture and 2.5 μl DNB polymerase II were added to each tube, mixed by a vortex shaker for 5 seconds, centrifuged briefly, and then placed in the PCR instrument at 30° C. for 20 minutes, with the hot lid set as a temperature of 60° C.

4.1.3 After the step 4.1.2, 20 μl DNB Stop Buffer was added to each tube, blew gently with a wide-mouth pipette and mixed for 20 times to terminate the reaction.

4.1.4 After the step 4.1.3, the concentration of DNB generated was detected through the Qubit ssDNA Assay produced by Invitrogen according to the instruments, in which the concentration greater than 10 ng/μl is qualified.

4.2 Loading of DNB

After preparation, the DNBs were loaded on a chip, that is, loading of DNB.

Loading of DNB was conducted according to the specific steps as below:

A sample loading reagent plate V2.1 was taken to room temperature for melting, mixed under shaking, briefly centrifuged and placed on ice for use. DNB loading buffer II was taken, shaked for uniformity, briefly centrifuged and placed on ice for use. A chip and the sample loading reagent plate V2.1 were placed in the BGIDL-50. 35 μl of DNB loading buffer II was added to a PCR tube containing 100 μl DNB, gently mixed for 15 times with a wide-mouth pipette and arranged in a designated DNB area of the loading system. Loading process was initiated via the DNB loading program (Sample load 2.0), and the loaded chip was incubated at room temperature for 30 minutes and then stored at 2-8° C. for use.

4.3 On-Machine Test

The protein to be tested was subjected to on-machine sequencing on the BGI SEQ-500 sequencer by using a chip and a BGISEQ-500RS high-throughput sequencing reagent tank (PE50 V2.0). Before the on-machine sequencing, sequencing reagent tank II, dNTPs mixture (V3.0) and dNTPs mixture II (V2.0) were thawed and placed in a refrigerator or ice box at 4° C. for use; and the DNA polymerase for sequencing was mixed under shaking and placed in an ice box for use. Specifically, a reagent for No. 5 well was formulated, that is, 1150 μl DNA polymerase mixture and 1150 μl dNTPs mixture (V3.0) were respectively transferred into the No. 5 well with a 1 ml pipette, and blew with the pipette for 10 to 15 times for uniformity; a reagent for No. 6 well was formulated, that is, 890 μl DNA polymerase mixture and 890 μl dNTPs mixture II (V2.0) were respectively transferred into the No. 6 well with a 1 ml pipette, and blew with the pipette for 10 to 15 times for uniformity; and a reagent for No. 14 well was formulated, that is, all reagent for the No. 14 well was taken with a 5 ml pipette, and 2.8 ml of the reagent for the No. 14 well and 400 μl phi29 polymerase mutant were mixed and transferred into this well. After that, those well-prepared reagent tanks were assembled. Finally, the on-machine sequencing was conducted, that is, initiating the sequencer, washing, placing the reagent tank in a designated position of the sequencer, pre-loading according to the operation sequence, assembling the chip prepared in step 4.2 after the pre-loading, filling in corresponding sequencing information, and starting the sequencing. After the completion of sequencing, the chip and reagent tank were removed, and the machine was washed.

4.4 Data Analysis

After the completion of sequencing, the analysis report was downloaded, and the performance of phi29 DNA polymerase mutants was evaluated according to previously specified criteria. For this, the wild-type phi29 DNA polymerase and its mutants were tested. Results in the example are shown in Table 4, in which the series number of mutants in Table 4 corresponds to that in Table 3. From the sequencing quality parameter AvgErrorRate %, mutants 97K-123I-515P and 97K-123H-515P are of the lowest value, followed by mutant 97A-123F-515G, and then mutants 97A-123H-515G and 97A-123H-515P, in contrast the wild-type phi29 DNA polymerase exhibits worst performance. In addition, the mutants in the example all have a value of parameter MappingRate % higher than that of wild-type phi29 DNA polymerase.

TABLE 4

| Series number of mutant | | NO. 1 | | NO. 3 | | NO. 4 | | NO. 5 | | NO. 6 | | NO. 7 | |
|---|---|---|---|---|---|---|---|---|---|---|---|---|---|
| Sequencing quality parameter | Standard | rep.1 | rep.2 | rep.1 | rep.2 | rep.1 | rep.2 | rep.1 | rep.2 | rep.1 | rep.2 | rep.1 | rep.2 |
| ESR % | ≥80 | 81 | 79.73 | 84 | 82 | 84 | 83 | 79 | 81 | 88 | 86 | 88 | 88 |
| Q30% | ≥88 | 86 | 88.46 | 89 | 89 | 89 | 89 | 88 | 88 | 91 | 91 | 91 | 91 |
| Mapping Rate % | ≥98 | 98.53 | 98.86 | 99 | 99 | 99 | 99 | 99 | 99 | 99 | 99 | 100 | 100 |
| AvgErrorRate % | ≤0.46 | 1.12 | 0.83 | 0.33 | 0.23 | 0.2 | 0.21 | 0.26 | 0.24 | 0.21 | 0.21 | 0.11 | 0.12 |

ESR (effective spot rate) represents the ratio of total number of Reads to total number of DNBs on the chip;

Q30 represents the ratio of bases with a quality value greater than 30 to the total base number;

Mapping Rate represents the ratio of number of Reads mapped to the reference sequence to total Reads number;

AvgError Rate represents average base error rate relative to the reference sequence.

INDUSTRIAL APPLICATION

The phi29 DNA polymerase in the prior art (i.e. wild-type phi29 DNA polymerase) has a poor thermal stability, thus resulting in a short shelf life of product and limited downstream application. The present disclosure has screened out several mutants with significantly improved thermal stability from large numbers of phi29 DNA polymerase mutants by using site-directed mutagenesis technology. On basis of the present disclosure, a mutant having a good effect can be further selected by subjecting the amino acids at the mutation sites of the present disclosure to a saturation mutation. Alternatively, on basis of the mutant of the present disclosure, similar effects can be achieved by mutating other amino acids except for the mutation sites included in the present disclosure. The mutant protein provided in the present disclosure has significantly improved thermal stability compared to the wild-type protein, which can greatly extend the shelf life of product and effectively improve the sequencing effect of the sequencing platform (such as, BGISEQ-500). Such mutant proteins can exist in the form of separately packaged DNA polymerase product or can be packaged in a DNA amplification kit or a DNA sequencing kit. The present disclosure also can be used in technical fields of food detection, virus detection, RNA detection, single cell sequencing and the like, as well as development of third or fourth generation sequencers.

What is claimed is:

1. A protein obtained by subjecting the phi29 DNA polymerase of SEQ ID NO: 1 to substitutions, wherein the protein comprises all of SEQ ID NO: 1 except for:
   (i) the substitution of amino acid residue Methionine at position 97 of the polypeptide of SEQ ID NO: 1 with Histidine, Alanine, or Lysine;
   (ii) the substitution of amino acid residue Leucine at position 123 of the polypeptide of SEQ ID NO: 1 with Lysine, Phenylalanine, Isoleucine, or Histidine; and
   (iii) the substitution of amino acid residue Glutamic acid at position 515 of the polypeptide of SEQ ID NO: 1 with Glycine or Proline,
   wherein the protein maintains DNA polymerase activity and has increased thermal stability compared to the phi29 DNA polymerase of SEQ ID NO: 1.

2. The protein according to claim 1, wherein the protein is selected from the group consisting of:
   (a) a protein that comprises all of SEQ ID NO: 1 except for the substitutions of amino acid residue Methionine at position 97 with Alanine, Leucine at position 123 with Histidine and Glutamic acid at position 515 with Proline;
   (b) a protein that comprises all of SEQ ID NO: 1 except for the substitutions of amino acid residue Methionine at position 97 with Lysine, Leucine at position 123 with Isoleucine and Glutamic acid at position 515 with Proline;
   (c) a protein that comprises all of SEQ ID NO: 1 except for the substitutions of amino acid residue Methionine at position 97 with Lysine, Leucine (L) at position 123 with Phenylalanine and Glutamic acid at position 515 with Proline;
   (d) a protein that comprises all of SEQ ID NO: 1 except for the substitutions of amino acid residue Methionine at position 97 with Lysine, Leucine at position 123 with Histidine and Glutamic acid at position 515 with Proline;
   (e) a protein that comprises all of SEQ ID NO: 1 except for the substitutions of amino acid residue Methionine at position 97 with Lysine, Leucine at position 123 with Lysine and Glutamic acid at position 515 with Proline;
   (f) a protein that comprises all of SEQ ID NO: 1 except for the substitutions of amino acid residue Methionine at position 97 with Alanine, Leucine at position 123 with Phenylalanine and Glutamic acid at position 515 with Glycine;
   (g) a protein that comprises all of SEQ ID NO: 1 except for the substitutions of amino acid residue Methionine at position 97 with Lysine, Leucine at position 123 with Histidine and Glutamic acid at position 515 with Glycine;
   (h) a protein that comprises all of SEQ ID NO: 1 except for the substitutions of amino acid residue Methionine at position 97 with Lysine, Leucine at position 123 with Isoleucine and Glutamic acid at position 515 with Glycine;
   (i) a protein that comprises all of SEQ ID NO: 1 except for the substitutions of amino acid residue Methionine at position 97 with Alanine, Leucine at position 123 with Histidine and Glutamic acid at position 515 with Glycine;
   (g) a protein that comprises all of SEQ ID NO: 1 except for the substitutions of amino acid residue Methionine at position 97 with Histidine, Leucine at position 123 with Isoleucine and Glutamic acid at position 515 with Glycine;
   (k) a protein that comprises all of SEQ ID NO: 1 except for the substitutions of amino acid residue Methionine at position 97 with Histidine, Leucine at position 123 with Histidine and Glutamic acid at position 515 with Glycine.

3. A kit, comprising the protein of claim 1.

4. A method of improving the stability of phi29 DNA polymerase, comprising subjecting the phi29 DNA polymerase of SEQ ID NO:1 to substitutions, wherein the protein obtained by subjecting the phi29 DNA polymerase of SEQ ID NO:1 to substitutions comprises all of SEQ ID NO:1 except for:
- (i) the substitution of amino acid residue Methionine at position 97 of the polypeptide of SEQ ID NO: 1 with Histidine, Alanine, or Lysine;
- (ii) the substitution of amino acid residue Leucine at position 123 of the polypeptide of SEQ ID NO: 1 with Lysine, Phenylalanine, Isoleucine, or Histidine; and
- (iii) the substitution of amino acid residue Glutamic acid at position 515 of the polypeptide of SEQ ID NO: 1 with Glycine or Proline.

5. The method according to claim 4, wherein the stability is thermal stability.

* * * * *